US010725128B2

(12) United States Patent
Zink

(10) Patent No.: US 10,725,128 B2
(45) Date of Patent: Jul. 28, 2020

(54) ADJUSTABLE LOCAL COIL ARRANGEMENT

(71) Applicant: Stephan Zink, Erlangen (DE)

(72) Inventor: Stephan Zink, Erlangen (DE)

(73) Assignee: Siemens Healthcare GmbH, Erlangen (DE)

(*) Notice: Subject to any disclaimer, the term of this patent is extended or adjusted under 35 U.S.C. 154(b) by 101 days.

(21) Appl. No.: 15/962,490

(22) Filed: Apr. 25, 2018

(65) Prior Publication Data

US 2018/0313915 A1 Nov. 1, 2018

(30) Foreign Application Priority Data

Apr. 26, 2017 (EP) .................................... 17168190

(51) Int. Cl.
*G01R 33/34* (2006.01)
*A61B 5/055* (2006.01)
*G01R 33/3415* (2006.01)

(52) U.S. Cl.
CPC ........ *G01R 33/34084* (2013.01); *A61B 5/055* (2013.01); *G01R 33/3415* (2013.01);
(Continued)

(58) Field of Classification Search
CPC ........ G01R 33/34084; G01R 33/34046; G01R 33/34092; G01R 33/3415; A61B 5/055
See application file for complete search history.

(56) References Cited

U.S. PATENT DOCUMENTS 5,543,711 A * 8/1996 Srinivasan ....... G01R 33/34046
324/318
6,011,393 A * 1/2000 Kaufman ......... G01R 33/34046
324/318
(Continued)

FOREIGN PATENT DOCUMENTS

CN 1959428 A 5/2007
CN 101297213 A 10/2008
(Continued)

OTHER PUBLICATIONS

European Search Report for corresponding Application No. 17168190.1-1914 / 3187889, dated Oct. 19, 2017.
(Continued)

*Primary Examiner* — Dixomara Vargas
(74) *Attorney, Agent, or Firm* — Lempia Summerfield Katz LLC

(57) ABSTRACT

A local coil arrangement and a magnetic resonance apparatus are provided for examining an examination object by magnetic resonance. A local coil arrangement includes at least a first coil unit and a second coil unit and at least a first intermediary unit. In an assembled state, the first intermediary unit is arranged between the first coil unit and the second coil unit. The first coil unit, the second coil unit and the first intermediary unit enclose at least partially an object receiving region for accommodating the examination object. The object receiving region includes a central axis. The shape and/or size of the object receiving region may be changed by relative movements of the first coil unit, of the second coil unit and of the first intermediary unit perpendicular to the central axis.

12 Claims, 6 Drawing Sheets

(52) U.S. Cl.
CPC . *G01R 33/34046* (2013.01); *G01R 33/34092* (2013.01); *G01R 33/34007* (2013.01)

(56) References Cited

U.S. PATENT DOCUMENTS

| | | | | |
|---|---|---|---|---|
| 6,577,887 | B2 * | 6/2003 | Wolff | A61B 5/0555 600/411 |
| 6,577,888 | B1 * | 6/2003 | Chan | A61B 5/0555 324/318 |
| 6,975,115 | B1 | 12/2005 | Fujita et al. | |
| 7,212,002 | B2 * | 5/2007 | Greim | G01R 33/341 324/318 |
| 7,315,167 | B2 * | 1/2008 | Bottcher | G01R 33/34046 324/318 |
| 7,646,199 | B2 * | 1/2010 | Dannels | G01R 33/34007 324/307 |
| 2005/0174117 | A1 * | 8/2005 | Greim | G01R 33/341 324/318 |
| 2007/0103153 | A1 * | 5/2007 | Bottcher | G01R 33/34046 324/300 |
| 2007/0103157 | A1 | 5/2007 | Campagna | |
| 2008/0007259 | A1 | 1/2008 | Driemel | |
| 2008/0204021 | A1 * | 8/2008 | Leussler | G01R 33/3415 324/318 |
| 2008/0211498 | A1 * | 9/2008 | Dannels | G01R 33/34007 324/309 |
| 2008/0265890 | A1 | 10/2008 | Graesslin | |
| 2010/0060284 | A1 * | 3/2010 | Sugiura | G01R 33/3664 324/318 |
| 2010/0280360 | A1 | 11/2010 | Wang | |
| 2011/0226260 | A1 | 9/2011 | Eder | |
| 2012/0256633 | A1 | 10/2012 | Biber et al. | |
| 2013/0307535 | A1 * | 11/2013 | Taracila | G01R 33/3415 324/307 |
| 2013/0307540 | A1 * | 11/2013 | Taracila | G01R 33/34007 324/318 |
| 2013/0317346 | A1 | 11/2013 | Alagappan | |
| 2014/0005525 | A1 | 1/2014 | Chen | |
| 2014/0191757 | A1 * | 7/2014 | Randell | G01R 33/34007 324/322 |
| 2015/0293188 | A1 | 10/2015 | Haider et al. | |
| 2016/0054404 | A1 | 2/2016 | Duensing | |
| 2016/0077172 | A1 * | 3/2016 | Duensing | G01R 33/34007 600/422 |
| 2016/0135711 | A1 * | 5/2016 | Dohata | A61B 5/0555 600/422 |
| 2016/0161577 | A1 * | 6/2016 | Taracila | G01R 33/34007 324/309 |
| 2016/0238677 | A1 * | 8/2016 | Fischer | G01R 33/36 |
| 2016/0363642 | A1 | 12/2016 | Gall et al. | |
| 2018/0017643 | A1 | 1/2018 | Zink | |

FOREIGN PATENT DOCUMENTS

| | | |
|---|---|---|
| CN | 101874731 A | 11/2010 |
| CN | 203149102 U | 8/2013 |
| CN | 103513198 A | 1/2014 |
| CN | 105074489 A | 11/2015 |
| DE | 102006027189 A1 | 12/2007 |
| DE | 102011007065 A1 | 10/2012 |
| DE | 102013105273 A1 | 11/2013 |
| DE | 102014207020 A1 | 10/2015 |
| DE | 102015210529 A1 | 12/2016 |
| DE | 102016212724 B4 | 1/2018 |

OTHER PUBLICATIONS

Chinese Office Action for Chinese Application No. 201810383850.2 dated Apr. 23, 2019.
European Office Action for European Patent Application No. 17 168 190.1-1210, dated Jan. 18, 2018, with English Translation.

* cited by examiner

ADJUSTABLE LOCAL COIL ARRANGEMENT

CROSS REFERENCE TO RELATED APPLICATIONS

This application claims the benefit of EP17168190.1 filed on Apr. 26, 2017, which is hereby incorporated by reference in its entirety.

FIELD

Embodiments relate to a local coil arrangement and to a magnetic resonance apparatus.

BACKGROUND

Imaging techniques are an important tool in medical technology. For example, magnetic resonance (MR) may be used to produce clinical sectional images that have high and variable soft tissue contrasts. One or more MR coil apparatuses may be used, that include one or more magnetic resonance antennas, referred to as coil elements, for transmitting and/or receiving high frequency electromagnetic signals.

Special MR coil apparatuses, for example, local coil arrangements, may be used for MR imaging of peripheral body regions such as joints in arms and legs. It is desirable that such a local coil arrangement may be adjusted optimally to the size and/or shape of the examined parts of the body. A good filling factor, that the adjustment makes achievable, and/or a minimized spatial distance between examination object and coil elements, that the local coil arrangement includes, provides for an improvement in the signal-to-noise ratio and in the image quality. If the local coil arrangement is configured to be too big, the image noise increases. If the local coil arrangement is too small in design the arrangement may impair patient comfort, for instance by exerting an unpleasant pressure, or the arrangement may not be usable at all.

The known local coil arrangements may be classified as rigid types configured to fit the body region and as flexible types. Rigid local coil arrangements that are often used for head examinations for instance, are optimally configured to fit an average patient anatomy, so as to include as many patients as possible (usually 95% percentile). For patients with small or intermediate anatomy dimensions, however, the best possible image quality is not achieved for reception because the coil elements do not lie optimally close to the body of the patient.

Flexible local coil arrangements may compensate for the lack of adjustment often only by accepting bulges and protrusions of portions of the local coil arrangement. For example for cylindrical body shapes such as knees and elbows, the coil elements normally have a different overlap or a different gap that limits the image quality that may be achieved. For example, the unexamined German application DE 10 2011 007 065 A1 describes a knee coil including a rigid part and a flexible part. The unexamined German application DE 10 2006 027 189 A1 discloses a local coil arrangement that may be varied in both height and width. The unexamined German application DE 10 2015 210 529 A1 discloses a local coil arrangement including an adjustable supporting structure including a plurality of support members that form a closed chain.

SUMMARY AND DESCRIPTION

The scope of the present disclosure is defined solely by the appended claims and is not affected to any degree by the statements within this summary The present embodiments may obviate one or more of the drawbacks or limitations in the related art.

Embodiments provide a magnetic resonance coil apparatus for improved image quality in magnetic resonance imaging while providing high patient comfort.

A local coil arrangement for examining an examination object, for example, a substantially cylindrical part of the body such as a knee, by magnetic resonance is provided. A local coil arrangement includes at least a first coil unit and a second coil unit and at least a first intermediary unit. The local coil arrangement may also include one or more further coil units in addition to the first and second coil units. The local coil arrangement may also include one or more further intermediary units, for example a second intermediary unit, in addition to the first intermediary unit.

In an assembled state, the first intermediary unit is arranged between the first coil unit and the second coil unit. For example, coil units and intermediary units are consistently arranged alternately, e.g. along a circumference in the following sequence: first coil unit, first intermediary unit, second coil unit and second intermediary unit, that is then followed again by the first coil unit.

The first coil unit, the second coil unit and the first intermediary unit enclose at least partially an object receiving region for accommodating the examination object. The object receiving region may include a central axis. The object receiving region is configured to position and/or support therein an examination object for an MR examination. The object receiving region may be dimensioned to accommodate a knee, for example, as the examination object. The local coil arrangement may be configured to be closed in a circumferential direction, for example if the local coil arrangement also includes a second intermediary unit, and/or to be open on one or two sides in the direction of the central axis, for instance in order to support a knee in the object receiving region.

The shape and/or size of the object receiving region may be changed by relative movements of the first coil unit, of the second coil unit and of the first intermediary unit perpendicular to the central axis. A direction perpendicular to an axis is also referred to as a radial direction. For each of the relative movements, at least one component of each relative movement, for example, the entire relative movement, is oriented perpendicular to the central unit, e.g. radially. The relative movement may also include, in addition to the component perpendicular to the central axis, another component parallel to the central axis. A direction parallel to an axis is often also referred to as an axial direction.

The movements of the first coil unit, of the second coil unit and of the first intermediary unit are thus performed relative to the central axis in a direction perpendicular to the central axis. The shape and/or size of the object receiving region changes if the first coil unit, the second coil unit and the first intermediary unit, and a possible second intermediary unit, are moved perpendicular to the central axis. The local coil arrangement may be adjusted to the individual anatomy of the examination object. For example, the local coil arrangement may be adjusted to a shape and/or size of the object receiving region in a cross-sectional plane perpendicular to the central axis. The local coil arrangement may be used both for thick and for thin knee shapes.

The first coil unit, the second coil unit, the first intermediary unit and a possible second intermediary unit are arranged such that the units may move relative to one another. For movements relative to the central axis, the units perform movements not only relative to the central axis but also relative to one another. The first coil unit and the first intermediary unit move relative to one another in a first displacement direction. The second coil unit and the first intermediary unit move relative to one another in a second displacement direction.

The relative movements of the first coil unit, of the second coil unit and of the first intermediary unit are coupled, for example positively coupled and/or guided. A relative movement of the first coil unit perpendicular to the central axis is thus accompanied by additional relative movements of the second coil unit and of the first intermediary unit perpendicular to the central axis. By the coupling of the relative movements relative to the central axis, the object receiving region may be adjusted in a defined and/or reproducible manner.

For relative movements of the first coil unit, of the second coil unit, of the first intermediary unit and of a possible second intermediary unit perpendicular to the central axis, the distances between the central axis and the first coil unit, the central axis and the second coil unit, the central axis and the first intermediary unit and the central axis and the possible second intermediary unit change in the same sense, e.g. for an increase in a distance between the first coil unit and the central axis, distances between the second coil unit and the central axis, between the first intermediary unit and the central axis and between the possible second intermediary unit and the central axis also increase, and/or for a decrease in a distance between the first coil unit and the central axis, distances between the second coil unit and the central axis, between the first intermediary unit and the central axis and between the possible second intermediary unit and the central axis also decrease. According to an embodiment, the distances of the first coil unit and second coil unit from the central axis and/or of the first intermediary unit from the central axis, change not only in the same sense but also each by the same amount as a result of their relative movements.

In an example in which the first coil unit or the second coil unit or the first intermediary unit or the possible second intermediary unit is stationary in a space, e.g. for a fixed position with respect to a coordinate system and/or inertial system of the space, given a relative movement, the central axis moves in the space, resulting in a change in the position of the central axis with respect to the coordinate system and/or inertial system.

The first coil unit and the first intermediary unit may include respective center planes that intersect in the central axis. The local coil arrangement is configured such that the relative movements of the first coil unit and of the first intermediary unit perpendicular to the central axis are performed parallel to the respective center planes, e.g. the relative movement of the first coil unit is thus made parallel to the center plane of the first coil unit, and the relative movement of the first intermediary unit is made parallel to the center plane of the first intermediary unit that allows for the shape and/or size of the object receiving region to be adjusted in a controlled and uniform manner.

At least one of the center planes may be a plane of symmetry, e.g. the first coil unit and/or the first intermediary unit is configured to be symmetric about its center plane. Also any further coil units and/or intermediary units may be configured to be symmetric with respect to a corresponding center plane that allows for a simple configuration of the local coil arrangement.

The first coil unit and/or the second coil unit and/or the first intermediary unit are configured to be rigid, for example stiff, flexurally stiff, inflexible and/or inelastic. Also any further coil units and/or intermediary units may be configured to be rigid, for example, stiff, flexurally stiff, inflexible and/or inelastic. The change in the shape and/or size of the object receiving region is thus achieved not by changing the shape of the first coil unit and/or of the second coil unit and/or of the first intermediary unit, but by the unit's movement relative to one another that allows for a high degree of control of the properties of the local coil arrangement when there is a change in shape and/or size.

The local coil arrangement includes a first part and a second part. The first part includes the first coil unit and the first intermediary unit, the second part includes the second coil unit, and the first part may be detached from the second part. The first part and/or the second part may also include possible further coil units and/or intermediary units. The local coil arrangement may be converted from an assembled state to a disassembled state. For example, the first part is an anterior part of the local coil arrangement and the second part is a posterior part of the local coil arrangement. In the disassembled state, the examination object may be positioned comfortably because, for example, a knee may be placed into a posterior part of a knee coil without the anterior part getting in the way during the process.

The first coil unit and/or the second coil unit and/or the first intermediary unit may include at least a portion of a magnetic resonance antenna, for example, of a receive antenna, also often referred to as an RX antenna. For example, the first coil unit includes a first portion of a first magnetic resonance antenna, and the second coil unit includes a first portion of a second magnetic resonance antenna, and the first intermediary unit includes a second portion of the first magnetic resonance antenna and a second portion of the second magnetic resonance antenna. The first portion and the second portion of the first magnetic resonance antenna, and the first portion and the second portion of the second magnetic resonance antenna, for example, in an assembled state, in each case function as a magnetic resonance antenna, for example, a complete magnetic resonance antenna.

If the local coil arrangement includes further coil units and/or intermediary units, that may include at least a portion of a magnetic resonance antenna. The coil units and/or intermediary unit may also include a plurality of magnetic resonance antennas.

A magnetic resonance antenna may include an electrical loop that may be connected to an electrical circuit that is configure, for example, to receive magnetic resonance signals and/or to transmit excitation signals. A portion of a magnetic resonance antenna may include, for example, a portion of an electrical loop, e.g. may include a half-loop. Two portions of a magnetic resonance antenna may be combined to form a magnetic resonance antenna, for example, a complete magnetic resonance antenna.

The first intermediary unit may include a first contact unit and a second contact unit. In addition, the first coil unit and the second coil unit each include at least one further contact unit. The first contact unit of the first intermediary unit may be arranged on the at least one further contact unit of the first coil unit, and the second contact unit of the first intermediary unit may be arranged on the at least one further contact unit of the second coil unit. The first intermediary unit may move relative to the first coil unit and to the second coil unit along the contact units that may be arranged against one another.

The at least one further contact unit may correspond to the first or second contact unit so that the units mate with one another. The contact units may include, for example, points and/or surfaces that interact, e.g. touch one another, at least in an assembled state.

The first intermediary unit may be movably connected to the first coil unit and the second coil unit with the aid of the contact units. At least one electrical contact and/or at least one mechanical contact may be made between the first intermediary unit and the first coil unit and/or the second coil unit by the contact units.

Electrical signals may be transmitted. For example, portions of an electrical loop, e.g. portions that may be a magnetic resonance antenna, may be connected to one another by the at least one electrical contact.

The first intermediary unit may include a first portion of a magnetic resonance antenna, and the first coil unit includes a second portion of the magnetic resonance antenna. The first portion and the second portion of the magnetic resonance antenna may be connected by the first contact unit of the first intermediary unit and by the at least one further contact unit of the first coil unit. A magnetic resonance antenna may extend over a plurality of units of the local coil arrangement that improves the coverage of the examination object by the measuring equipment and increases the signal-to-noise ratio.

By the at least one mechanical contact it is possible, for instance, to transfer between the first intermediary unit and the first coil unit and/or the second coil unit mechanical forces that assist, for example, guide, the relative movements of the first coil unit, of the second coil unit and of the first intermediary unit perpendicular to the central axis.

The first contact unit of the first intermediary unit and the further contact unit of the first coil unit may include a mating mechanical guidance mechanism that guides the relative movements at least partially. The first contact unit of the first intermediary unit and the further contact unit of the second coil unit may include a mating mechanical guidance mechanism that guides the relative movements at least partially. A mechanical guidance mechanism of the type may include an interlocking rail system, for example.

The at least one further contact unit of the first coil unit and/or of the second coil unit may each have a surface that is inclined with respect to a direction of the movement relative to the central axis, for example with respect to the perpendicular component of the movement relative to the central axis, that is made by the first intermediary unit, by an angle of inclination. The angle of inclination is greater than 0° and less than 90°. For example, the angle of inclination is greater than 10° and less than 80°, the angle of inclination is greater than 20° and less than 70°, the angle of inclination is greater than 30° and less than 60°, the angle of inclination is greater than 40° and less than 50°, or the angle of inclination is substantially 45°.

The angle of inclination corresponds to the coupling of the relative movements relative to the central axis. An angle of inclination of 45° may correspond to relative movements of the first coil unit, of the second coil unit and of the first intermediary unit perpendicular to the central axis in which the distances between the central axis and the first coil unit, the second coil unit and the first intermediary unit change by an equal amount. The selection of the angle of inclination may be used to adjust how the shape of the local coil arrangement in a cross-sectional plane perpendicular to the central axis changes for a relative movement of the first coil unit, of the second coil unit and of the first intermediary unit.

The surface of the at least one further contact unit of the first coil unit and/or of the second coil unit may be located respectively on the side of the first coil unit and/or of the second coil unit that faces the central axis. The surface of the at least one further contact unit of the first coil unit and/or of the second coil unit may bound the object receiving region.

The first contact unit and/or the second contact unit of the first intermediary unit includes a surface that, in an assembled state of the local coil arrangement, faces, runs parallel to, the surface of the at least one further contact unit of the first coil unit and/or of the second coil unit.

First contact unit and/or the second contact unit and/or the at least one further contact unit may include at least one contact surface. The at least one contact surface may be arranged on the surface of the at least one further contact unit of the first coil unit and/or of the second coil unit.

The first contact unit and the second contact unit of the first intermediary unit, and the at least one further contact unit of the first coil unit and respectively of the second coil unit, each may include an electrical connecting element that may be used to make the electrical contact between the first intermediary unit and the first coil unit and/or the second coil unit in order to connect together portions of a magnetic resonance antenna, for example.

The electrical connecting element of the first contact unit and/or of the second contact unit of the first intermediary unit and/or of the at least one further contact unit of the first coil unit and/or of the second coil unit may include at least one land for receiving a mating contact. A land may refer to an electrically conducting surface on which an electrically conducting mating contact, e.g. a pin, may be positioned to close an electrical circuit.

The mating contact may include at least one spring-loaded contact and/or ball contact and/or sliding contact. Reliable electrical connections may be made by the contact variants. For example, a spring-loaded contact may correct for manufacturing tolerances.

The electrical connecting element of the first contact unit and/or of the second contact unit of the first intermediary unit and/or of the at least one further contact unit of the first coil unit and/or of the second coil unit includes a plurality of lands for receiving a mating contact, the plurality of lands being arranged linearly along the first or second displacement direction. Such an arrangement of the plurality of lands allows, for example, the size of the electrical loops to be changed while simultaneously ensuring that electrical contact is made.

The electrical connecting element of the first contact unit and/or of the second contact unit of the first intermediary unit and/or of the at least one further contact unit of the first coil unit and/or of the second coil unit includes at least one correction circuit. The electrical connecting element is configured to activate the at least one correction circuit according to contact made with the plurality of lands by the mating contact. a matched correction circuit, for example, matched to the size of the resultant loop, takes effect depending on which of the plurality of lands makes contact with the mating contact. The quality of any magnetic resonance signals received by the loop may thereby be increased.

According to an embodiment of the local coil arrangement, the local coil arrangement includes a second intermediary unit. In an assembled state the second intermediary unit is arranged between the first coil unit and the second coil unit. The first intermediary unit and the second intermediary unit are arranged on opposite sides of the local coil arrangement from each other. The arrangement constitutes a simple configuration of the local coil arrangement. It is thereby possible to alter the local coil arrangement both in terms of height by changing the distance between the first coil unit and the second coil unit, and in terms of width by changing the distance between the first intermediary unit and the second intermediary unit.

The local coil arrangement includes a plurality of intermediary units and a plurality of coil units. The number of the plurality of intermediary units equals the number of the plurality of coil units. In an assembled state, each intermediary unit is arranged between two coil units.

The local coil arrangement includes a housing with an external surface that is configured such that the external surface's shape and size remain unchanged when there are relative movements of the first coil unit, of the second coil unit and of the first intermediary unit perpendicular to the central axis. The external surface is arranged on a side of the local coil arrangement that faces away from the central axis.

The housing includes at least one magnetic resonance antenna for transmitting RF signals. RF signals refer to high frequency electromagnetic signals for exciting atomic nuclei in the examination object.

A magnetic resonance apparatus is also proposed including at least one local coil arrangement.

DETAILED DESCRIPTION

Figure 1:
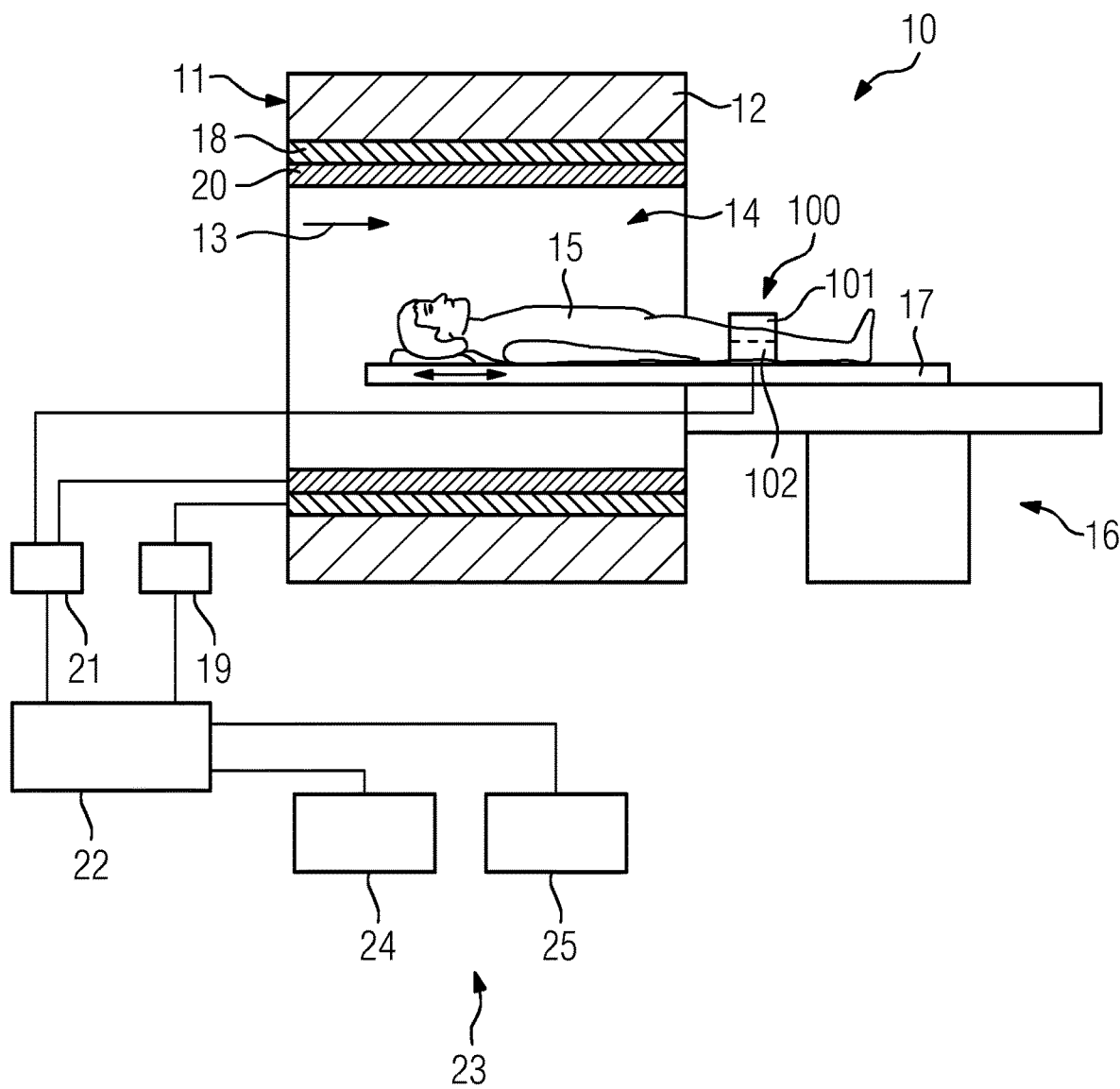
FIG. 1 depicts an example schematic view of a magnetic resonance apparatus including a local coil arrangement.

FIG. 1 depicts schematically a magnetic resonance apparatus 10. The magnetic resonance apparatus 10 includes a magnet unit 11, that contains a main magnet 12 for producing a powerful main magnetic field 13 that, for example, is constant over time. The magnetic resonance apparatus 10 also includes a patient receiving region 14 for accommodating a patient 15. In an embodiment, the patient receiving region 14 is shaped as a cylinder and is enclosed in a circumferential direction cylindrically by the magnet unit 11. The patient receiving region 14 may include a different design. The patient 15 may be moved into the patient receiving region 14 by a patient support apparatus 16 of the magnetic resonance apparatus 10. The patient support apparatus 16 includes a patient couch 17, that is configured to be able to move inside the patient receiving region 14.

The magnet unit 11 further includes a gradient coil unit 18 for generating magnetic field gradients, that are used for spatial encoding during imaging. The gradient coil unit 18 is controlled by a gradient control unit 19 of the magnetic resonance apparatus 10. The magnet unit 11 also includes an RF antenna unit 20, that is configured as a body coil that is permanently built into the magnetic resonance apparatus 10. The RF antenna unit 20 is configured to excite atomic nuclei, whose excitation is established in the main magnetic field 13 produced by the main magnet 12. The RF antenna unit 20 is controlled by an RF antenna control unit 21 of the magnetic resonance apparatus 10 and radiates high frequency magnetic resonance sequences into an examination space, that is largely formed by a patient receiving region 14 of the magnetic resonance apparatus 10. The RF antenna unit 20 is also configured to receive magnetic resonance signals.

The magnetic resonance apparatus 10 includes a system control unit 22 for controlling the main magnet 12, the gradient control unit 19 and the RF antenna control unit 21. The system control unit 22 centrally controls the magnetic resonance apparatus 10, for instance implementing a predetermined imaging gradient echo sequence. In addition, the system control unit 22 includes an analysis unit (not shown in further detail) for analyzing medical image data acquired during the magnetic resonance examination. In addition, the magnetic resonance apparatus 10 includes a user interface 23, that is connected to the system control unit 22. Control information such as imaging parameters, for instance, and reconstructed magnetic resonance images may be displayed to medical personnel on a display unit 24, for example on at least one monitor, of the user interface 23. In addition, the user interface 23 includes an input unit 25, that may be used by the medical operating personnel to enter data and/or parameters during a measurement process.

In the example, a knee of the patient 15 is the examination object, for which purpose a local coil arrangement 100 is arranged on the knee for examining the examination object by magnetic resonance. The local coil arrangement 100 is configured, for example, to receive magnetic resonance signals and to transfer the signals to the RF antenna control unit 21 for further processing.

In the example, the local coil arrangement 100 includes a first (anterior) part 101 and a second (posterior) part 102. The first part 101 is configured to be detachable from the second part 102 so that the knee may be placed comfortably on the second part 102 in a disassembled state, and the first part 101 may be mounted on the second part in order to produce the assembled state of the local coil arrangement, which state is shown in FIG. 1. A continuous local coil arrangement may be opened in order to position a part of the body, and then re-closed.

Figure 2:
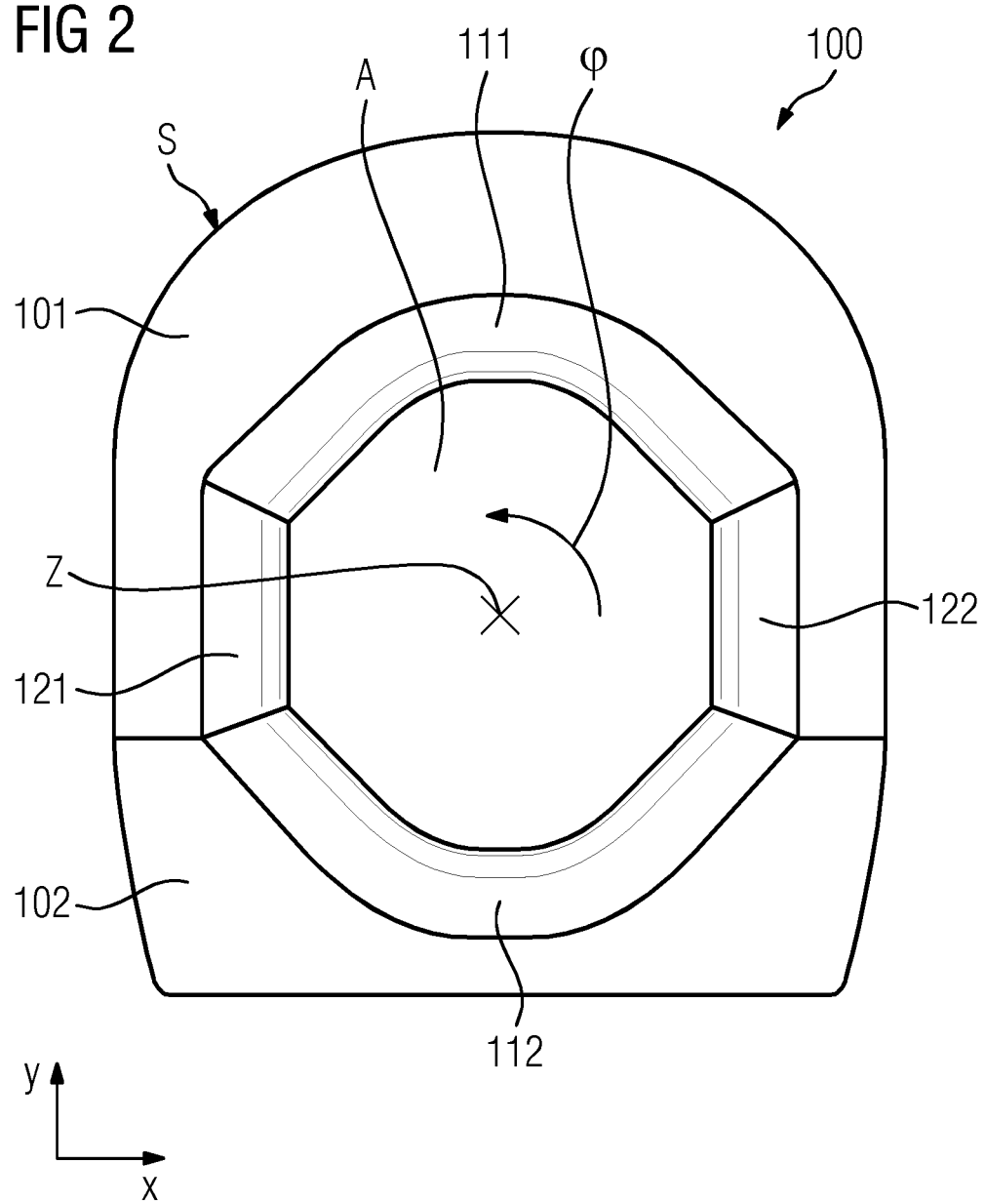
FIG. 2 depicts an example local coil arrangement including a larger object receiving region.
Figure 3:
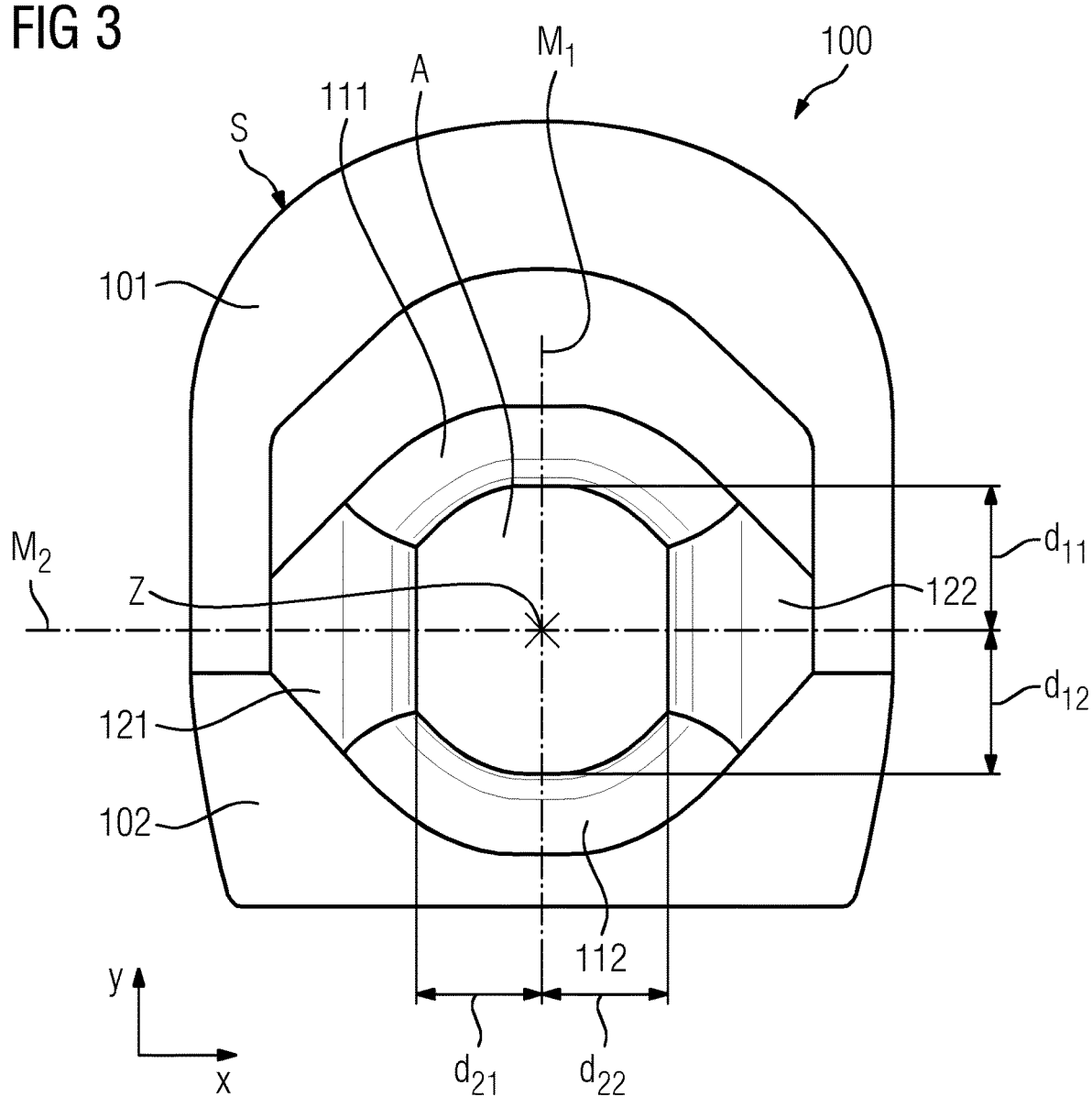
FIG. 3 depicts an example local coil arrangement including a smaller object receiving region.
Figure 4:
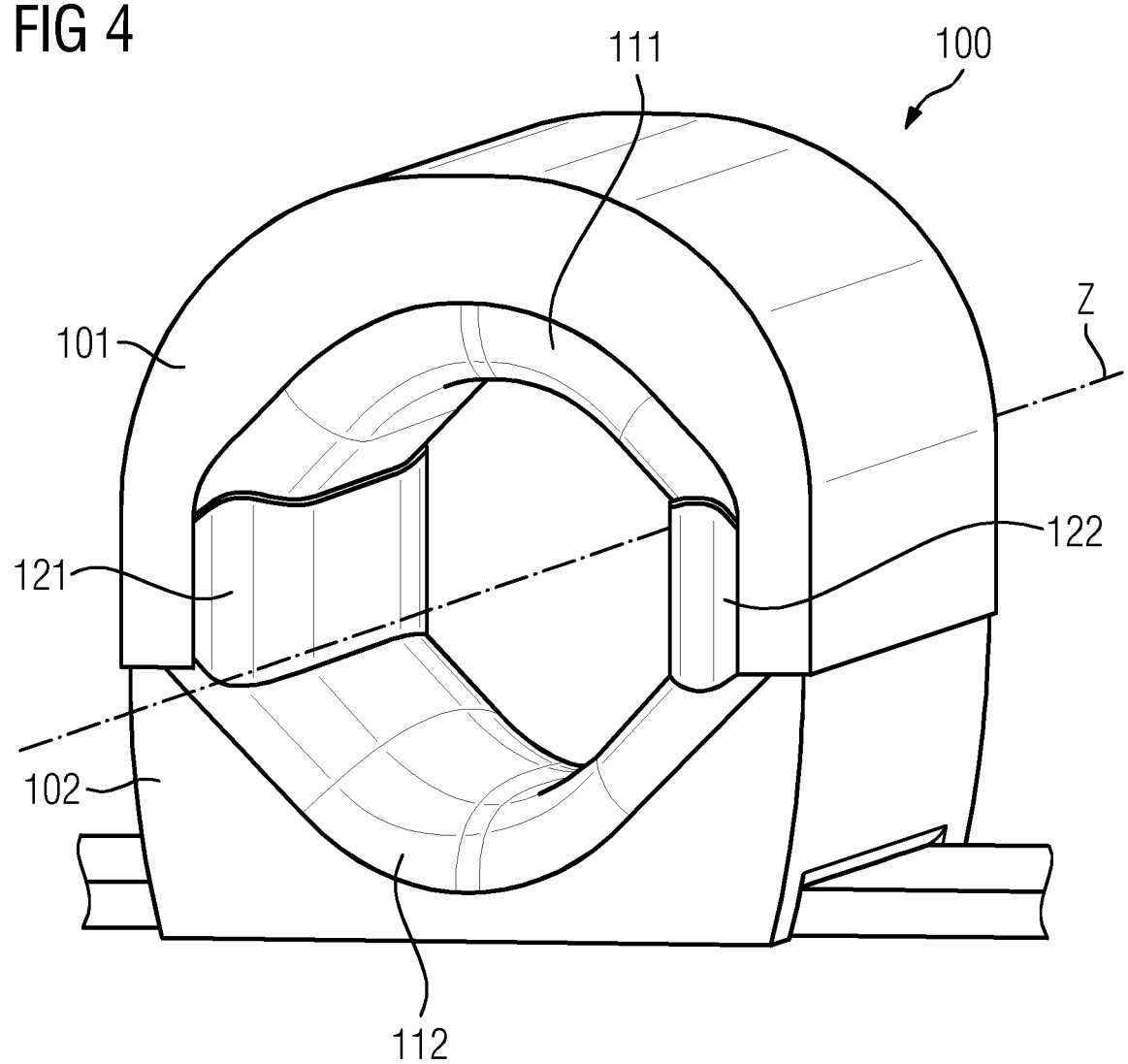
FIG. 4 depicts a perspective view of a local coil arrangement according to an embodiment.

FIGS. 2, 3 and 4 show by way of example the local coil arrangement 100 in an assembled state with FIG. 4 showing a perspective view. The local coil arrangement 100 includes a first coil unit 111 and a second coil unit 112, a first intermediary unit 121 and a second intermediary unit 122. The first part 101 includes the first coil unit 111 and the first intermediary unit 121 (as with the second intermediary unit 122), and the second part 102 of the local coil arrangement 100 includes the second coil unit 112.

In an assembled state, the first intermediary unit 121 and the second intermediary unit 122 are each arranged between the first coil unit 111 and the second coil unit 112, although on opposite sides of the local coil arrangement from each other.

The first coil unit 111, the second coil unit 112 and the first intermediary unit 121 enclose at least partially an object receiving region A for accommodating the examination object. Together with the second intermediary unit 122, the object receiving region A is completely enclosed in a circumferential direction φ. The object receiving region A includes a central axis Z, that in the diagram of FIG. 2 and FIG. 3 is oriented perpendicular to the drawing plane.

Comparing FIG. 2 with FIG. 3 reveals that the shape and/or size of the object receiving region A may be changed by relative movements of the first coil unit 111, of the second coil unit 112 and of the first intermediary unit 121 perpendicular to the central axis Z. The change in the object receiving region A is made here by a relative movement of the first coil unit 111 in a direction perpendicular to the central axis, by an additional relative movement of the second coil unit 112 in a direction perpendicular to the central axis, and by an additional relative movement of the first intermediary unit 121 in a direction perpendicular to the central axis. In addition, the second intermediary unit 122 also moves in a direction perpendicular to the central axis.

In relation to an xy-coordinate system that is fixed with respect to the second part 102, the coordinates of the central axis Z change as a result of the relative movements of the first coil unit 111, of the second coil unit 112 and of the first intermediary unit 121. In relation to the xy-coordinate system, the second coil unit 112 remains static, whereas the first coil unit 111 moves (upwards or downwards) along the y-axis. In the downwards movement, the first coil unit 111 takes with it the first intermediary unit 121 and the second intermediary unit 122, resulting in the relative movements described above of the first coil unit 111, of the first intermediary unit 121 and of the second intermediary unit 122 relative to the central axis Z.

In addition, for relative movements of the first coil unit 111, of the second coil unit 112, of the first intermediary unit 121 and of the second intermediary unit 122 perpendicular to the central axis Z, the distances $d_{11}$, $d_{12}$, $d_{21}$, $d_{22}$ between the central axis Z and the first coil unit 111, the central axis Z and the second coil unit 112, the central axis Z and the first intermediary unit 121 and between the central axis X and the second intermediary unit 122 change in the same sense, i.e. either all the distances $d_{11}$, $d_{12}$, $d_{21}$ become larger or all the distances $d_{11}$, $d_{12}$, $d_{21}$ become smaller. Examination objects of different diameters may thereby be enclosed in as close a fit as possible. For example, a same size and/or shape of the object receiving region A may be set for repeat measurements of the same patient 15, with the result that the magnetic resonance measurement that may thereby be performed is reproducible.

The first coil unit 111 includes a center plane $M_1$, and the first intermediary unit includes a center plane $M_2$. The center planes $M_1$ and $M_2$ intersect in the central axis Z. The relative movements of the first coil unit 111 and of the first intermediary unit 121 perpendicular to the central axis Z, that, for example, result in the change in the shape and/or size of the object receiving region, are performed parallel to the respective center planes, e.g. the relative movement of the first coil unit 111 is performed parallel to the center plane $M_1$, and the relative movement of the first coil unit 121 is performed parallel to the center plane $M_2$.

By the mechanism for adjusting the object receiving region A, the boundary of the object receiving region A moves into regions in which there is still free space. Pinching, trapping and even soiling may hence be avoided. The workflow is also simplified because, in addition to adjusting the object receiving region A, it is also possible at the same time to fix the examination object by the internal surface of the local coil arrangement 100, which surface bounds the object receiving region A. The more or less adjustable size also provides for functional imaging. In addition, the local coil arrangement 100 may be used in a versatile way, because the local coil arrangement 100 may be adjusted to different geometries of the examination object (e.g. large and small knee, bandages, different angles of joints, etc.).

The local coil arrangement 100 includes a housing including an external surface S that is configured such that its shape and size remain unchanged when there are relative movements of the first coil unit 111, of the second coil unit 112 and of the first intermediary unit 121 perpendicular to the central axis Z. The shape of the enclosure of the local coil arrangement 100 thus always stays the same irrespective of the adjustment of the object receiving region A, and therefore only the interior is adjusted in the process. It is hence possible, for example, to implement magnetic resonance antennas for transmitting RF signals, often also known as TX antennas, so that the antennas do not alter their position relative to the xy-coordinate system. It is also possible, however, that the magnetic resonance antennas are implemented such that the antennas are repositioned with a change in the object receiving region A.

Figure 5:
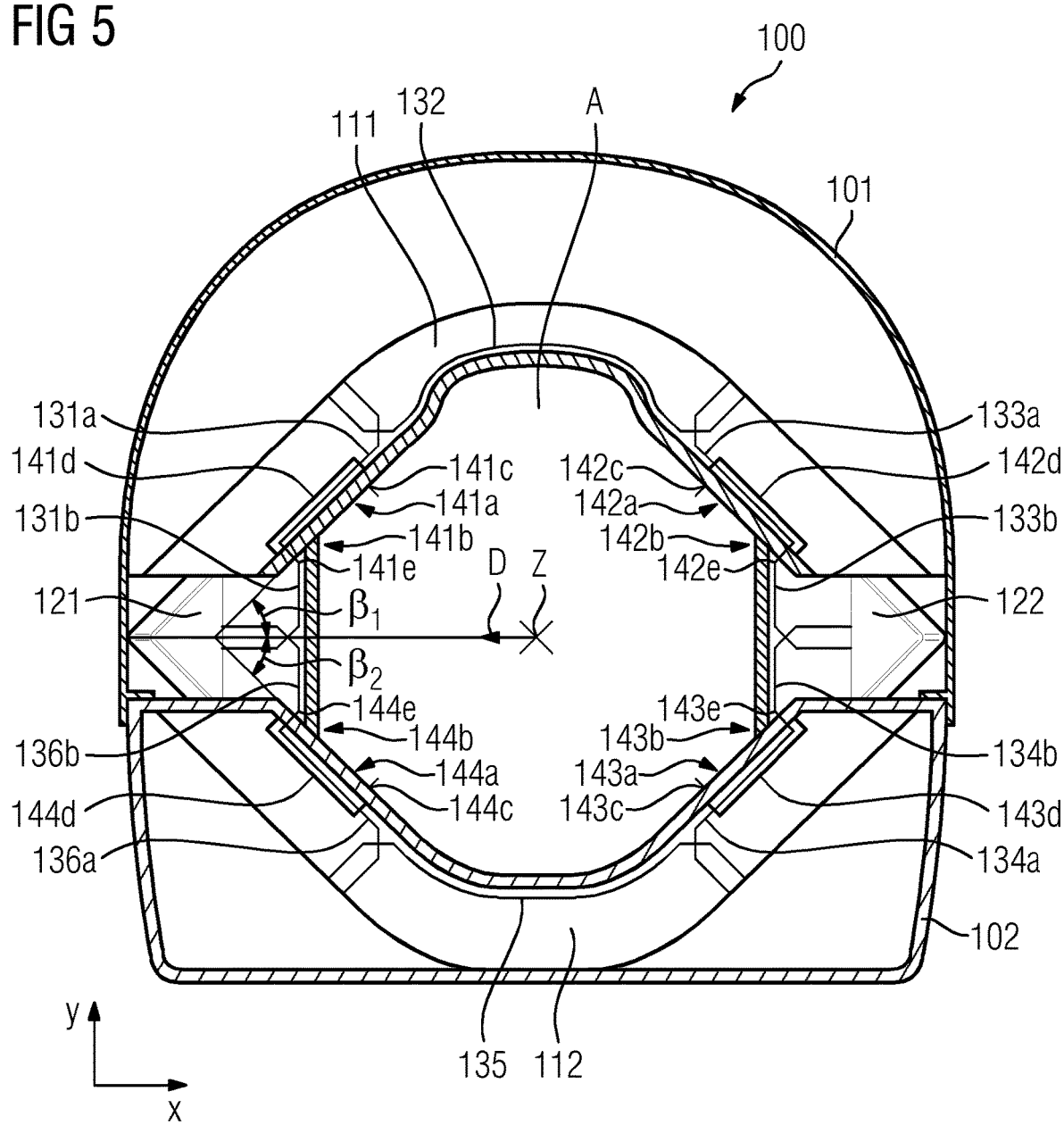
FIG. 5 depicts a cross-sectional view of a local coil arrangement according to an embodiment.

FIG. 5 shows in cross-section an example of a local coil arrangement 100. The first intermediary unit 121 includes a first contact unit 141b and a second contact unit 144b. The second intermediary unit 122 includes a contact unit 142b and a contact unit 143b. The first coil unit 111 includes further contact units 141a and 142a. The second coil unit 112 includes further contact units 143a and 144a. The first contact unit 141b of the first intermediary unit 121 is arranged on the contact unit 141a of the first coil unit 111. The second contact unit 144b of the first intermediary unit 121 is arranged on the contact unit 144a of the second coil unit 112. The intermediary unit 121 may move relative to the first coil unit 111 and the second coil unit 112 along the contact units, that are arranged against one another, as was also already illustrated with reference to FIGS. 2 and 3.

The contact unit 141a of the first coil unit 111 includes a surface 141c, and the contact unit 144a of the second coil unit 112 includes a surface 144c. The surface 141c is inclined with respect to a direction D of the movement of the first intermediary unit 121 relative to the central axis Z by an angle of inclination $\beta_1$. The angle of inclination $\beta_1$ is greater than 0° and less than 90°. The surface 144c is inclined with respect to the direction D of the movement of the first intermediary unit 121 relative to the central axis Z by an angle of inclination $\beta_2$. The angle of inclination $\beta_2$ is greater than 0° and less than 90°. $\beta_1$ is equal to $\beta_2$.

Adjustment directions may be favored and/or scaled selectively by the angle of inclination. For instance for an angle of 45°, the dimension of the object receiving region A in the x-direction (x-dimension, width), for example, changes by the same amount as the dimension of the object receiving region A in the y-direction (y-dimension, height). The larger the angle of inclination that is chosen, the greater the change in the y-dimension compared with the x-dimension.

The contact unit 141b may be moved on the surface 141c, and the contact unit 144b may be moved on the 144c. The contact unit 141b travels up and down on the inclined surface 141c. The same also applies to the surfaces 142c and 143c by their respective corresponding contact units 142b and 143b. The result is that the relative movements of the first coil unit 111, of the second coil unit 112 and of the first intermediary unit 121 perpendicular to the central axis Z are coupled.

A mechanism that is the mirror image exists with regard to the second intermediary unit 121 and the first coil unit 111 and respectively the second coil unit 112.

In FIG. 5, the first coil unit 111, the second coil unit 112 and the first intermediary unit 121 (as with the second intermediary unit 122) include at least a portion of a magnetic resonance antenna.

The first intermediary unit 121 includes a first portion 131b of a first magnetic resonance antenna 131, and a first portion 136b of a sixth magnetic resonance antenna 136. The second intermediary unit 122 includes a first portion 133b of a third magnetic resonance antenna 133, and a first portion 134b of a fourth magnetic resonance antenna 134.

The first coil unit 111 includes a second portion 131a of the first magnetic resonance antenna 131, a second magnetic resonance antenna 132, and a second portion 133a of the third magnetic resonance antenna 133. The second coil unit 112 includes a second portion 134a of the fourth magnetic resonance antenna 134, a fifth magnetic resonance antenna 135 and a second portion 136a of the sixth magnetic resonance antenna 136.

The first portion 131b and the second portion 131a of the first magnetic resonance antenna 131 may be connected by the first contact unit 141b of the first intermediary unit 121 and by the contact unit 141a of the first coil unit 111. In addition, the first portion 133b and the second portion 133a of the third magnetic resonance antenna 133 may be connected by the contact units 142b and 142a. In addition, the first portion 134b and the second portion 134a of the fourth magnetic resonance antenna 134 may be connected by the contact units 143b and 143a. In addition, the first portion 136b and the second portion 136a of the sixth magnetic resonance antenna 136 may be connected by the contact units 144b and 144a.

A local coil arrangement may also include more than or fewer than the six magnetic resonance antennas shown here by way of example.

By the mechanism described here for adjusting the object receiving region A, the divided magnetic resonance antennas 131, 133, 134, 136 may be changed reproducibly in terms of their shape and/or size. An undefined overlap or a gap may be avoided.

The first contact unit 141b of the first intermediary unit 121 includes an electrical connecting element 141e. The second contact unit 144b of the first intermediary unit 121 includes an electrical connecting element 144e. Similarly, the further contact units 141a, 142a, 143a, 144a of the first coil unit 111 and of the second coil unit 121 each include an electrical connecting element 141d, 142d, 143d, 144d respectively. Also the contact units 142b, 143b of the second intermediary unit 122 each include an electrical connecting element 142e, 143e respectively.

Figure 6:
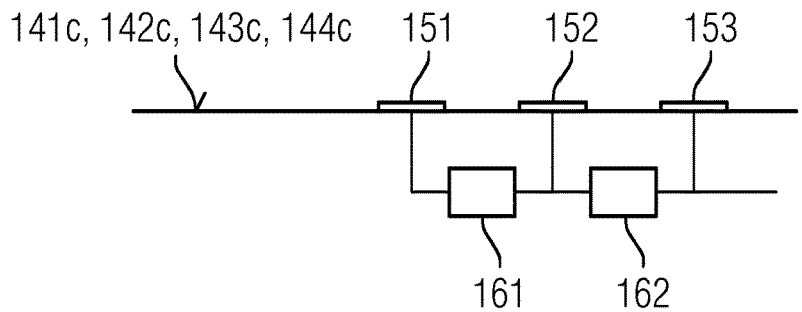
FIG. 6 depicts an electrical connecting element including series-connected correction circuits according to an embodiment.
Figure 7:
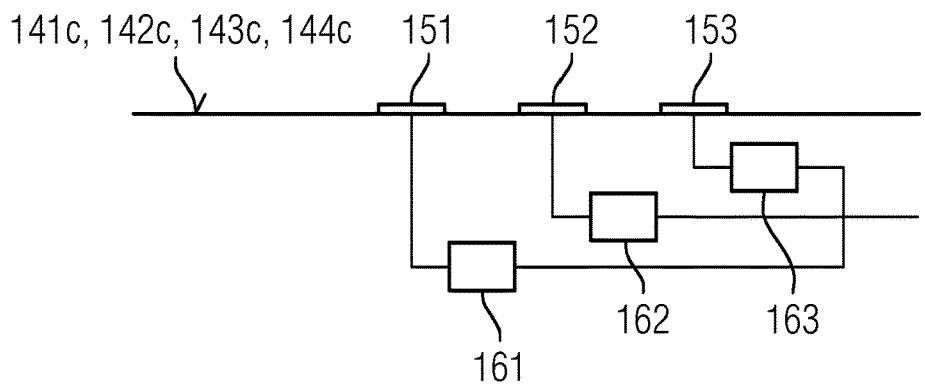
FIG. 7 depicts an electrical connecting element including parallel-connected correction circuits according to an embodiment.
Figure 8:
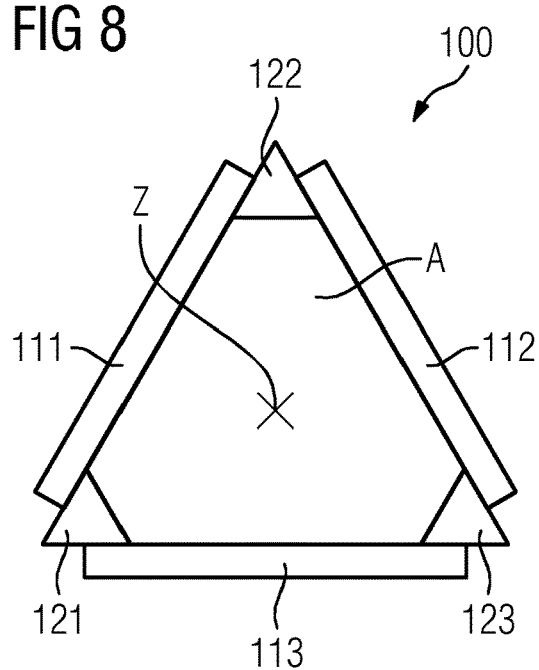
FIG. 8 depicts a schematic view of a local coil arrangement including three intermediary units and three coil units according to an embodiment.

FIGS. 6 and 7 show a schematic diagram of the electrical connecting elements 141d, 142d, 143d, 144d, that includes three lands 151, 152, 153 for receiving a mating contact. The lands 151, 152, 153 are arranged on the surfaces 141c, 142c, 142c, 142d of the contact units 141a, 142a, 143a, 144a. In FIG. 6, the lands 151, 152, 153 are connected to correction circuits 161, 162, that are connected in series. FIG. 7 shows another variant, in which the lands 151, 152, 153 are connected to correction circuits 161, 162, 163, that are connected in parallel.

Electrical connecting elements 141d, 142d, 143d, 144d are configured to activate one of the correction circuits 161, 162, 163 according to contact made with the plurality of lands by the mating contact. Thus if the mating contact makes contact with the land 151, the correction circuit 161 is activated; if the mating contact makes contact with the land 152, the correction circuit 163 is activated, and so on.

In an embodiment, the electrical connecting elements 141e, 144e, 142e, 143e of the first intermediary unit 121 and respectively of the second intermediary unit 122 each include a mating contact, for example, a spring-loaded sliding contact.

For a movement, for example, of the first intermediary unit 121 relative to the first coil unit 111, the electrical connecting element 141e, e.g. the spring-loaded sliding contact, moves along the surface 141c over the electrical connecting unit 141d, for example, over the lands 151, 152, 153. The size of the magnetic resonance antenna 131 also varies according to the adjustment of the shape and/or size of the object receiving region. The associated change in the tuning of the magnetic resonance antenna 131 is corrected by a correction circuit, that is achieved by the connecting element 141e making contact with precisely that land 151, 152 or 153 that activates the correction circuit 161, 162 or 163 configured for the correction.

The resizable magnetic resonance antennas 131, 133, 134, 136 of the local coil arrangement 100 may enclose a body region as the examination object with no losses or only minimal losses because the magnetic resonance antennas 131, 133, 134, 136 are always optimally matched for each shape and/or size of the object receiving region A.

FIG. 7 depicts an example where the adjustment mechanism shown in FIGS. 2 to 5 may also be applied to a larger number of coil units and intermediary units. The local coil arrangement 100 includes three coil units 111, 112, 113 and three intermediary units 121, 122, 123, that are respectively arranged between the coil units 111, 112, 113. Together the coil units 111, 112, 113 enclose an object receiving region A including a central axis Z.

It is to be understood that the elements and features recited in the appended claims may be combined in different ways to produce new claims that likewise fall within the scope of the present disclosure. Thus, whereas the dependent claims appended below depend from only a single independent or dependent claim, it is to be understood that these dependent claims may, alternatively, be made to depend in the alternative from any preceding or following claim, whether independent or dependent, and that such new combinations are to be understood as forming a part of the present specification.

While the present disclosure has been described above by reference to various embodiments, it may be understood that many changes and modifications may be made to the described embodiments. It is therefore intended that the foregoing description be regarded as illustrative rather than limiting, and that it be understood that all equivalents and/or combinations of embodiments are intended to be included in this description.

The invention claimed is:

1. A local coil arrangement for examining an examination object by magnetic resonance, the local coil arrangement comprising:
   at least a first coil unit and a second coil unit, wherein the first coil unit is rigid; and
   at least a rigid first intermediary unit,
      wherein in an assembled state, the first intermediary unit is arranged between the first coil unit and the second coil unit,
      wherein the first coil unit, the second coil unit, and the first intermediary unit enclose at least partially an object receiving region for accommodating the examination object,
      wherein the object receiving region includes a central axis,
      wherein the first coil unit, the second coil unit, the first intermediary unit, or any combination thereof comprises at least a portion of a magnetic resonance antenna;

wherein a shape and a size of the object receiving region is adjusted by relative movements between assembled states of the first coil unit, the second coil unit, the first intermediary unit, or any combination thereof;

wherein relative movements of the first coil unit, relative movements of the second coil unit, and relative movements of the first intermediary unit are configured such that: the shape, the size, or the shape and the size of the object receiving region are adjustable by relative movements of the first coil unit in a direction perpendicular to the central axis, relative movements of the second coil unit in the direction perpendicular to the central axis, and relative movements of the first intermediary unit in the direction perpendicular to the central axis; wherein the relative movements of the first coil unit, the relative movements of the second coil unit, and the relative movements of the first intermediary unit are performed relative to one another.

2. The local coil arrangement of claim 1, wherein for the relative movements of the first coil unit in the direction perpendicular to the central axis, the relative movements of the second coil unit in the direction perpendicular to the central axis, and the relative movements of the first intermediary unit in the direction perpendicular to the central axis, distances between the central axis and the first coil unit, distances between the central axis and the second coil unit, and distances between the central axis and the first intermediary unit change in the same way.

3. The local coil arrangement of claim 1, wherein the first coil unit and the first intermediary unit have respective center planes that intersect in the central axis, and wherein the relative movements of the first coil unit in the direction perpendicular to the central axis and the relative movements of the first intermediary unit in the direction perpendicular to the central axis are performed parallel to the respective center planes.

4. The local coil arrangement of claim 1, further comprising a first part and a second part, wherein the first part comprises the first coil unit and the first intermediary unit, wherein the second part comprises the second coil unit, and wherein the first part is detachable from the second part.

5. The local coil arrangement of claim 1, wherein the first intermediary unit comprises a first contact unit and a second contact unit, wherein the first coil unit and the second coil unit each comprise at least one further contact unit, wherein the first contact unit of the first intermediary unit is arrangeable on the at least one further contact unit of the first coil unit, and the second contact unit of the first intermediary unit is arrangeable on the at least one further contact unit of the second coil unit, and wherein the first intermediary unit is movable relative to the first coil unit and to the second coil unit along the first contact unit, the second contact unit, and the further contact unit, which are arrangeable against one another.

6. The local coil arrangement of claim 5, wherein the first intermediary unit comprises a first portion of a magnetic resonance antenna, and the first coil unit comprises a second portion of the magnetic resonance antenna, and wherein the first portion and the second portion of the magnetic resonance antenna are connectable by the first contact unit of the first intermediary unit and by the at least one further contact unit of the first coil unit.

7. The local coil arrangement of claim 5, wherein the at least one further contact unit of the first coil unit, of the second coil, or of the first coil unit and of the second coil each have a surface that is inclined with respect to a direction of the movement relative to the central axis made by the first intermediary unit by an angle of inclination, and wherein the angle of inclination is greater than 0° and less than 90°.

8. The local coil arrangement of claim 5, wherein the first contact unit, the second contact unit, or the first contact unit and the second contact unit of the first intermediary or the at least one further contact unit of the first coil unit and respectively of the second coil unit, each comprise an electrical connecting element.

9. The local coil arrangement of claim 8, wherein the electrical connecting element comprises at least one land for receiving a mating contact, and wherein the mating contact comprises a spring-loaded contact, a ball contact, a sliding contact, or any combination thereof.

10. The local coil arrangement of claim 8, wherein the electrical connecting element comprises a plurality of lands for receiving a mating contact and comprises at least one correction circuit, and wherein the electrical connecting element is configured to activate the at least one correction circuit according to contact made with the plurality of lands by the mating contact.

11. The local coil arrangement of claim 1, further comprising a second intermediary unit, wherein the second intermediary unit is arranged between the first coil unit and the second coil unit, and wherein the first intermediary unit and the second intermediary unit are arranged on opposite sides of the local coil arrangement from each other.

12. The local coil arrangement of claim 1, further comprising a housing including an external surface that is configured such that a shape and size remain unchanged when there are relative movements of the first coil unit, the second coil unit, and the first intermediary unit perpendicular to the central axis.

* * * * *